United States Patent
Overbeck et al.

(10) Patent No.: US 7,301,627 B2
(45) Date of Patent: Nov. 27, 2007

(54) SYSTEMS AND METHODS FOR MONITORING A PROCESS OUTPUT WITH A HIGHLY ABRIDGED SPECTROPHOTOMETER

(75) Inventors: James L. Overbeck, Ada, MI (US); Thomas Richardson, Ada, MI (US)

(73) Assignee: X-Rite, Inc., Grand Rapids, MI (US)

( * ) Notice: Subject to any disclaimer, the term of this patent is extended or adjusted under 35 U.S.C. 154(b) by 0 days.

(21) Appl. No.: 11/397,547

(22) Filed: Apr. 4, 2006

(65) Prior Publication Data

US 2006/0244960 A1 Nov. 2, 2006

Related U.S. Application Data

(60) Provisional application No. 60/668,346, filed on Apr. 5, 2005, provisional application No. 60/670,407, filed on Apr. 12, 2005.

(51) Int. Cl.
G01J 3/42 (2006.01)
(52) U.S. Cl. ....................................... 356/319
(58) Field of Classification Search ................. 356/319
See application file for complete search history.

(56) References Cited

U.S. PATENT DOCUMENTS

| | | |
|---|---|---|
| 4,413,276 A | 11/1983 | Hertz et al. |
| 4,558,786 A | 12/1985 | Lane |
| 4,566,797 A | 1/1986 | Kaffka et al. |
| 4,618,257 A | 10/1986 | Bayne et al. |
| 4,707,838 A | 11/1987 | Reule et al. |
| 4,797,609 A | 1/1989 | Yang |
| 5,072,128 A | 12/1991 | Hayano et al. |
| 5,132,736 A | 7/1992 | Muramatsu et al. |
| 5,137,364 A | 8/1992 | McCarthy |
| 5,311,293 A | 5/1994 | MacFarlane et al. |
| 5,313,267 A | 5/1994 | MacFarlane et al. |
| 5,471,052 A | 11/1995 | Ryczek |
| 5,671,735 A | 9/1997 | MacFarlane et al. |
| 5,838,451 A | 11/1998 | McCarthy |
| 5,844,680 A | 12/1998 | Sperling |

(Continued)

FOREIGN PATENT DOCUMENTS

EP 0117606 A1 9/1984

(Continued)

OTHER PUBLICATIONS

International Search Report for PCT/US06/12416, Jan. 25, 2007 (4 pages).

(Continued)

*Primary Examiner*—Gregory J. Toatley, Jr.
*Assistant Examiner*—Kara Geisel
(74) *Attorney, Agent, or Firm*—McCarter & English, LLP

(57) ABSTRACT

A method for monitoring a process output with a highly abridged spectrophotometer. The method includes securing spectral data for each spectral primary used in a process, measuring spectral data with a highly abridged spectrophotometer for a sample produced by the process, determining an estimated weight for each spectral primary in the sample, and computing spectral data representative of the sample based on the secured spectral data and the determined estimated weight for each spectral primary in the sample.

22 Claims, 2 Drawing Sheets

U.S. PATENT DOCUMENTS

| | | | |
|---|---|---|---|
| 5,854,680 | A | 12/1998 | Rakitsch |
| 5,917,183 | A | 6/1999 | Sperling |
| 6,020,583 | A | 2/2000 | Walowit et al. |
| 6,067,504 | A | 5/2000 | MacFarlane et al. |
| 6,129,664 | A | 10/2000 | Macfarlane et al. |
| 6,147,761 | A | 11/2000 | Walowit et al. |
| 6,157,445 | A | 12/2000 | Macfarlane et al. |
| 6,178,341 | B1 | 1/2001 | Macfarlane et al. |
| 6,271,920 | B1 | 8/2001 | Macfarlane et al. |
| 6,308,088 | B1 | 10/2001 | MacFarlane et al. |
| 6,314,372 | B1 | 11/2001 | Macfarlane et al. |
| 6,330,341 | B1 | 12/2001 | Macfarlane et al. |
| 6,384,918 | B1 | 5/2002 | Hubble, III et al. |
| 6,400,099 | B1 | 6/2002 | Walker |
| 6,556,932 | B1 | 4/2003 | Mestha et al. |
| 6,577,395 | B1 | 6/2003 | Berns et al. |
| 6,584,435 | B2 | 6/2003 | Mestha et al. |
| 6,587,793 | B2 | 7/2003 | Viassolo et al. |
| 6,621,576 | B2 | 9/2003 | Tandon et al. |
| 6,653,992 | B1 | 11/2003 | Colbeth et al. |
| 6,661,513 | B1 | 12/2003 | Granger |
| 6,690,471 | B2 | 2/2004 | Tandon et al. |
| 6,721,692 | B2 | 4/2004 | Mestha et al. |
| 6,732,917 | B1 | 5/2004 | Benz et al. |
| 6,760,124 | B1 | 7/2004 | Boerger et al. |
| 6,765,674 | B2 | 7/2004 | Orelll et al. |
| 6,844,931 | B2 | 1/2005 | Ehbets |
| 6,903,813 | B2 | 6/2005 | Jung et al. |
| 7,027,186 | B2 * | 4/2006 | Sano et al. ........... 358/1.9 |
| 7,057,727 | B2 | 6/2006 | Ott |
| 7,113,281 | B2 | 9/2006 | Ott |
| 2003/0098896 | A1 | 5/2003 | Berns et al. |
| 2003/0197855 | A1* | 10/2003 | Jung et al. ........... 356/417 |
| 2004/0208210 | A1 | 10/2004 | Inoguchi |
| 2005/0036163 | A1* | 2/2005 | Edge ................... 358/1.9 |
| 2006/0244806 | A1 | 11/2006 | Overbeck et al. |
| 2006/0244935 | A1 | 11/2006 | Overbeck et al. |
| 2006/0244948 | A1 | 11/2006 | Overbeck |
| 2007/0035740 | A1 | 2/2007 | Nisper et al. |

FOREIGN PATENT DOCUMENTS

| | | | |
|---|---|---|---|
| EP | 0292957 | B1 | 4/1991 |
| EP | 0642012 | A1 | 3/1995 |
| EP | 0 696 867 | A2 | 2/1996 |
| EP | 0871025 | A1 | 10/1998 |
| EP | 1001393 | A2 | 5/2000 |
| EP | 1 291 628 | A2 | 3/2003 |
| EP | 1293762 | A2 | 3/2003 |
| EP | 1326199 | A2 | 7/2003 |
| EP | 0936400 | B1 | 3/2006 |
| GB | 1589335 | A | 5/1981 |
| JP | 59060324 | A | 4/1984 |
| JP | 2003185591 | A | 7/2003 |
| WO | WO98/11410 | A1 | 3/1998 |
| WO | WO 00/16045 | A1 | 3/2000 |
| WO | WO 01/16990 | A1 | 3/2001 |
| WO | WO 03/007663 | A1 | 1/2003 |
| WO | WO 03/083766 | A1 | 10/2003 |
| WO | WO 2004/056135 | A1 | 7/2004 |
| WO | WO 2005/013365 | A2 | 2/2005 |
| WO | WO 2005/050148 | A2 | 6/2005 |
| WO | WO 2005/114118 | A1 | 12/2005 |
| WO | WO 2006/020833 | A2 | 2/2006 |
| WO | WO 2006/053808 | A1 | 5/2006 |

OTHER PUBLICATIONS

E. J. Neugebauer, *Die Theoretischen Grundlagen des Mehrfarbenbuchdrucks (The Theoretical Foundation for Multicolor Printing)*, 36(4), pp. 73-89, 1937. Reprinted in Neugebauer Memorial Seminar on Color Reproduction, vol. 1184 of Proceedings of the SPIE, pp. 194-202. SPIE, Bellingham, WA, 1990.

U.S. Appl. No. 11/504,187, filed Aug. 15, 2006 (22 pages).

International Search Report for PCT/US2006/031891, Feb. 5, 2007 (8 pages).

International Search Report for PCT/US2006/031892, Feb. 16, 2007 (8 pages).

James H. Nobbs, "Colour-Match Prediction for Pigmented Materials," from *Colour Physics for Industry*, Chapter 6, pp. 292-372, (Roderick McDonald ed., Society of Dyers and Colurists, 2d ed. 1997).

Gunter Wyszecki & W.S. Stiles, *Color Science: Concepts and Methods, Quantitative Data and Formulae*, pp. 221-222, 785-786, (Joseph W. Goodman ed., John Wiley & Sons, Inc., 2d. ed. 1982).

Rolf G. Kuehni, Verona Division of Mobay Chemical Corp., *Computer Colorant Formulation*, Chapters 3-6, pp. 11-86, (Lexington Books 1975).

Paul Henry Hoffenberg, Automated Color-Matching of Printed Ink films (1972) (unpublished Ph.D. dissertation, Lehigh University) (on file with UMI Dissertation Information Service).

Raja Balasubramanian, *Optimization of the Spectral Neugebauer Model for Printer Characterization*, 8 Journal of electronic Imaging 156, 156-166 (1999).

Henry R. Kang, *Applications of Color Mixing Models to Electronic Printing*, 3 Journal of Electronic Imaging 276, 276-87 (1994).

R.D. Hersch et al., *Spectral Prediction and Dot Surface Estimation Models for Halftone Prints*, 5293 SPIE 356, 356-69 (2004).

Safer Mourad, Color Predicting Model for Electrophotographic Prints on Common Office Paper (2003) (unpublished M.S. thesis, Swiss Federal Institute of Technology), at htt://diwww.epfl.ch/w31sp/pub/papers/colour/thesis-mourad.pdf.

\* cited by examiner

SYSTEMS AND METHODS FOR MONITORING A PROCESS OUTPUT WITH A HIGHLY ABRIDGED SPECTROPHOTOMETER

CROSS-REFERENCE TO RELATED APPLICATIONS

This application claims the priority benefit of U.S. Provisional Patent Application No. 60/668,346, filed on Apr. 5, 2005 and U.S. Provisional Patent Application No. 60/670,407, filed on Apr. 12, 2005.

BACKGROUND

This application discloses an invention that is related, generally and in various embodiments, to systems and methods for monitoring a process output with a highly abridged spectrophotometer.

There are various types of spectrophotometers, and some are significantly more expensive than others. The relatively high cost of such devices is generally related to the number of measurements the spectrophotometer is configured to make over a given range of light wavelengths. For example, some of the more expensive spectrophotometers are scanning spectrophotometers which are configured to scan a constant bypass function across a given spectrum, thereby measuring reflectances at a multitude of different points across the spectrum. With some scanning spectrophotometers configured to scan at intervals of less than one nanometer (e.g., 0.2 nanometers), such scanning spectrophotometers provide a wealth of spectral data that may be used to generate a spectral curve that accurately represents the sample being measured. As known to those skilled in the art, spectral curves may be used in a number of applications. For example, spectral curves may be utilized to control the quality and consistency of a process output, to determine the color of a process output, etc. Although the accuracy generally provided by such scanning spectrophotometers can be useful in various applications, their initial expense is cost-prohibitive for many applications.

In some applications, to reduce the initial expense, a high-quality abridged spectrophotometer can be used in lieu of a scanning spectrophotometer. In general, abridged spectrophotometers measure reflectance of an object at a fixed number of points over a range of wavelengths of light. The number of points varies based on the cost and quality of the abridged spectrophotometer. If an abridged spectrophotometer measures reflectance at a significant number of points across a measured range of wavelengths, it can often perform quite similarly to a scanning spectrophotometer. For example, an abridged spectrophotometer that provides 128 spectral bands across the visual spectrum (e.g., approximately 400 nm to 700 nm) would provide spectral curves that reasonably approximate the spectral curves generated from a scanning spectrophotometer on most reflective surfaces. However, as the number of spectral bands is reduced, the agreement between the spectral curve produced by a scanning spectrophotometer and an abridged spectrophotometer begins to diverge. Also, if the object being measured has sharp spectral transitions, as would be the case for the measurement of didymium glass, the abridged spectrophotometer may fail to measure spectral information that falls between two measured wavelengths, thereby compromising the accuracy of the resulting spectral curve.

As manufacturers try to develop more affordable spectrophotometers, they often reduce the number of spectral bands measured to reduce the cost of the spectrophotometer. For example, an industry standard has developed whereby many abridged spectrophotometers manufactured today measure only thirty-one spectral bands across the visual spectrum. Although the spectral curves provided by such abridged spectrophotometers are generally acceptable for a number of applications, the initial expense of such abridged spectrophotometers is still cost-prohibitive for many applications.

To address the need for a low-cost abridged spectrophotometer, some manufacturers have developed highly abridged spectrophotometers that provide less than thirty-one spectral bands across the visual spectrum. These low-cost abridged instruments also may have uneven spacing of the bandpass filters across the measured spectrum as lower cost components are employed. The agreement of the spectral curves produced by the highly abridged spectrophotometers and higher quality spectrophotometers is relatively poor on most measured materials. Therefore, the highly abridged spectrophotometers are not currently being utilized in applications which require the level of accuracy generally provided by the higher quality spectrophotometers.

SUMMARY

In one general respect, this application discloses a method for monitoring a process output with an abridged spectrophotometer. According to various embodiments, the method comprises securing spectral data for each spectral primary used in a process, measuring spectral data with a highly abridged spectrophotometer for a sample produced by the process, determining an estimated weight for each spectral primary in the sample, and computing spectral data representative of the sample based on the secured spectral data and the determined estimated weight for each spectral primary in the sample.

In another general respect, this application discloses a system for monitoring a process output with a highly abridged spectrophotometer. According to various embodiments, the system comprises a highly abridged spectrophotometer, a mixing model module for determining an estimated weight for each spectral primary in a sample based on spectral data measured by the highly abridged spectrophotometer, and a spectral data computing module for computing spectral data representative of the sample based on the determined estimated weights.

Aspects of the disclosed invention may be implemented by a computer system and/or by a computer program stored on a computer readable medium. The computer readable medium may comprise a disk, a device, and/or a propagated signal.

Other features and advantages will be apparent from the following description, including the drawings, and from the claims.

DETAILED DESCRIPTION

The figures and descriptions of the disclosed invention have been simplified to illustrate elements that are relevant for a clear understanding of the disclosed invention. It should be understood that the methods, products, and systems described below may include various other processes, components, and elements in actual implementation.

Figure 1:
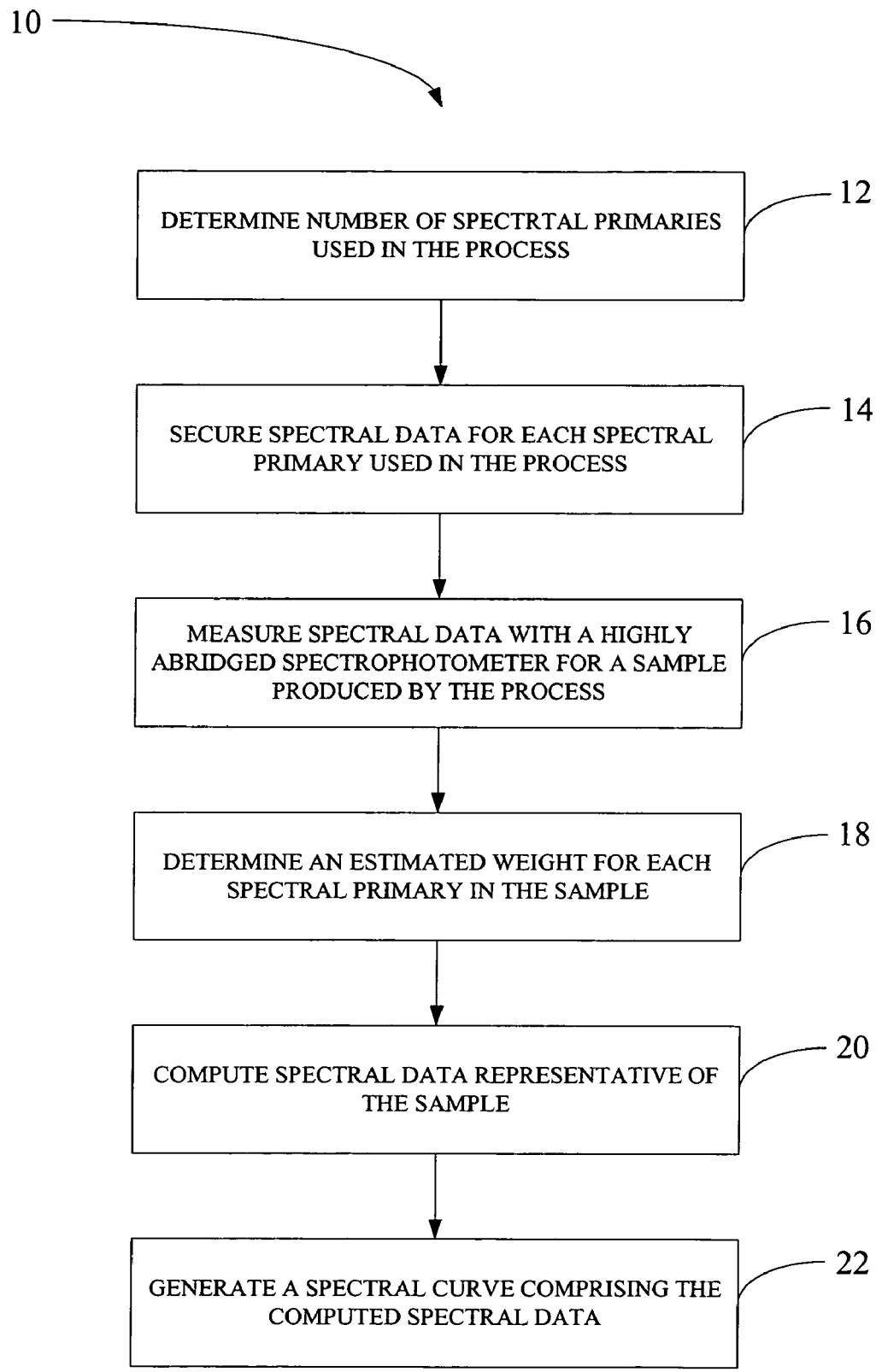
FIG. 1 illustrates various embodiments of a method for monitoring a process output with a highly abridged spectrophotometer.

FIG. 1 illustrates various embodiments of a method 10 for monitoring a process output with a highly abridged spectrophotometer. As used herein, the term highly abridged spectrophotometer generally refers to an abridged spectrophotometer that provides less than thirty-one spectral bands across the visual spectrum. The method 10 may be utilized with any number of different processes. For example, the method 10 may be utilized to monitor the production of food products, paints, plastics, printing (e.g., commercial ink jet, flexographic, gravure, lithographic printing, serigraphic printing, etc.), textiles, etc.

The method 10 starts at block 12, where a determination is made as to the number of spectral primaries used in a particular process. The determination may be realized in any number of different ways. For example, to determine the number of spectral primaries used by a particular ink jet printer, the determination can be made simply by looking at the number of ink cartridges in the printer. According to other embodiments, a measuring instrument such as, for example, a scanning spectrophotometer or an abridged spectrophotometer, may be utilized to measure a color bar present on a sample produced by the particular process in order to determine the number of spectral primaries used in the process.

According to yet other embodiments, the determination is made based on the particular process to be monitored. For many production process (e.g., inks on paper, phosphors in a CRT, dyes in a solution, process printing using halftones on paper, etc.), mixing models that predict the spectral curve associated with the process output are well known to those skilled in the art. Such mixing models include, for example, a Neugebauer model for predicting halftones in a lithographic printing process, a single constant Kubelka Munk model for textiles, a two constant Kubelka Munk model for paint mixing, a log absorbance model for transparent films, a multi-flux model for ink mixtures on paper, etc. For production processes having known mixing models associated therewith, the number of spectral primaries used in the process may be determined based on an appropriate mixing model.

From block 12, the method advances to block 14, where spectral data is secured for each spectral primary used in the process. According to various embodiments, a manufacturer of the ink, dye, colorant, etc. used in the process may simply provide the spectral data of the ink, dye, colorant, etc. for use as described hereinbelow. According to other embodiments, a benchmark instrument may be utilized to measure spectral data for each spectral primary used in the process. The benchmark instrument may be embodied, for example, as a scanning spectrophotometer, a high quality abridged spectrophotometer, etc. The measurement of the spectral data may take place at any location. For example, the measurement of the spectral data may take place at a location associated with the manufacturer of the inks, dyes, colorants, etc. utilized in the process. The secured spectral data may be recorded and stored for later use. The recorded spectral data may be stored at any location.

From block 14, the method advances to block 16, where a highly abridged spectrophotometer is utilized to measure spectral data for a sample produced by the process. The highly abridged spectrophotometer may measure the spectral data at any number of wavelengths across the visible spectrum. For example, according to various embodiments, the highly abridged spectrophotometer may measure the spectral data at 10 different wavelengths across the visual spectrum. The highly abridged spectrophotometer may be utilized to measure spectral data for any number of samples produced by the particular process. The spectral data measured by the highly abridged spectrophotometer may be recorded and stored for later use. The recorded data may be stored at the highly abridged spectrophotometer or external to the highly abridged spectrophotometer.

From block 16, the method advances to block 18, where a mixing model determines the estimated weight (i.e., relative mixture) of each spectral primary present in the sample. The mixing model may be embodied as a software application as described in more detail hereinbelow. The number of spectral primaries in the sample may be less than, equal to, or greater than the number of spectral primaries used in the particular production process. For example, as two or more of the spectral primaries used in the production process may mix to form a different spectral primary in the sample, the number of spectral primaries in the sample may be greater than the number of spectral primaries used in the particular process. The estimated weights determined at block 18 may be recorded and stored for later use. The recorded estimated weights may be stored at any location.

According to various embodiments, each spectral primary in the sample may be determined based on the spectral data measured by the highly abridged spectrophotometer at block 16. According to other embodiments, each spectral primary in the sample may be determined by measuring a color bar that is present on the sample, where the color bar includes each of the spectral primaries present in the sample.

From block 18, the method advances to block 20, where spectral data representative of the sample is computed. The computed spectral data is based on the estimated weight of each spectral primary in the sample and on the spectral data secured at block 14. Although the spectral data measured at block 16 with the highly abridged spectrophotometer and the spectral data computed at block 20 will generally be similar, the computed spectral data may not necessarily coincide with the spectral data measured by the highly abridged spectrophotometer. The computed spectral data may be recorded and stored for later use. The recorded computed spectral data may be stored at the highly abridged spectrophotometer or external to the highly abridged spectrophotometer.

From block 20, the method advances to block 22, where a spectral curve comprising the computed spectral data is generated. The computed spectral curve is representative of the sample produced by the particular process. From the foregoing, one skilled in the art will appreciate that the method 10 leverages the physics of color mixing to predict what spectra can exist in the sample produced by the particular process.

The spectral curve generated at block 22 (based in part on the spectral data measured by the highly abridged spectrophotometer) accurately approximates a spectral curve of the sample taken with a high-quality abridged spectrophotometer. With the above-described method 10, a highly abridged spectrophotometer measuring ten spectral bands across the visual spectrum may be utilized in lieu of the industry standard thirty-one spectral band device at block 16 to measure the spectral data of the sample with no discernable loss in accuracy.

Figure 2:
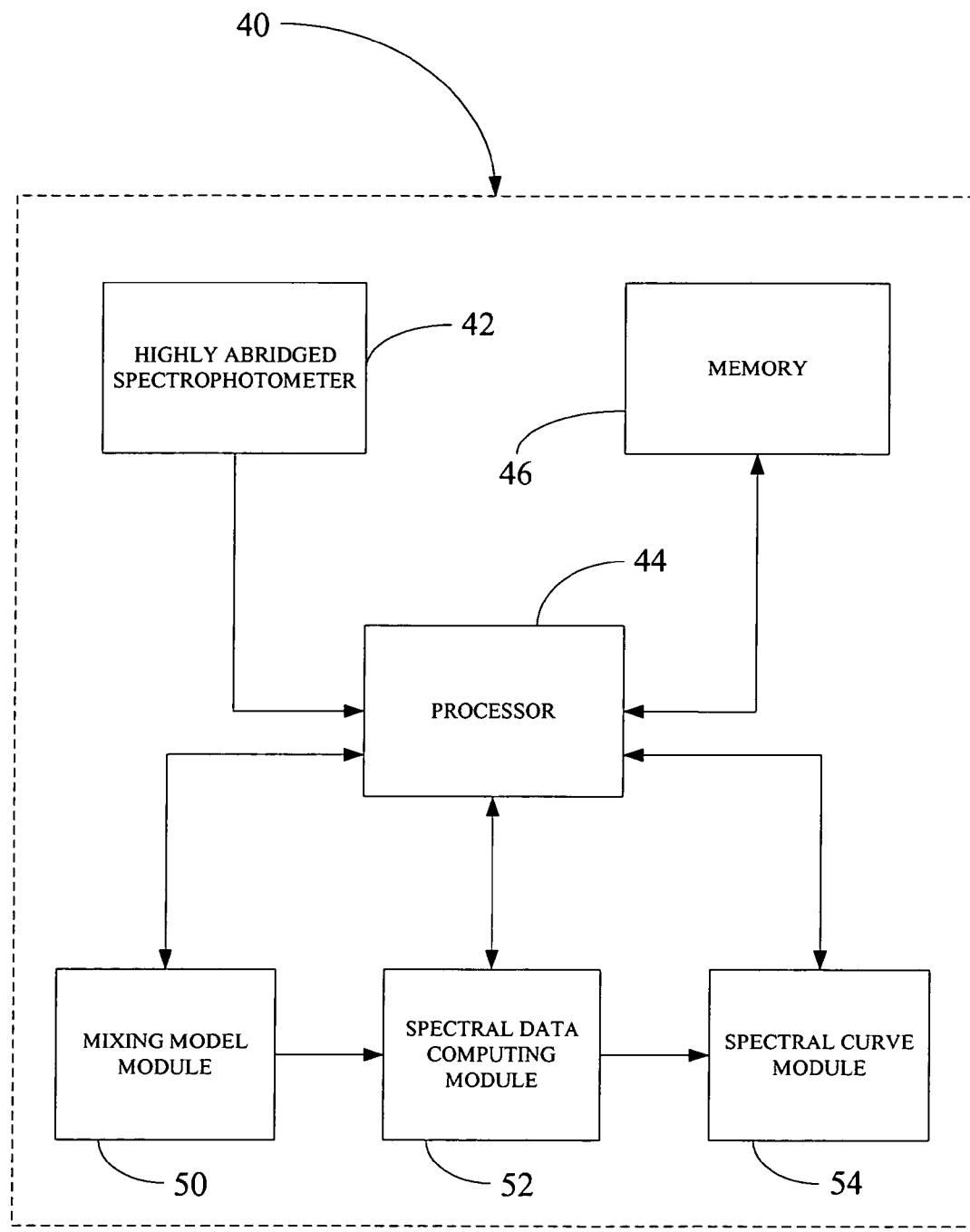
FIG. 2 illustrates various embodiments of a system for monitoring a process output with a highly abridged spectrophotometer.

FIG. 2 illustrates various embodiments of a system 40 for monitoring a process output with an abridged spectrophotometer 42. In general, one or more elements of the system 40 may perform the method 10 as described above.

The system 40 includes a highly abridged spectrophotometer 42, a processor 44, a memory 46, a mixing model module 48, and a spectral data computing module 50. According to various embodiments, one or more of the processor 44, the memory 46, the mixing model module 48, and the spectral data computing module 50 may comprise a portion of the highly abridged spectrophotometer 42. According to other embodiments, one or more of the processor 44, the memory 46, the mixing model module 48, and the spectral data computing module 50 may be separate and apart from the highly abridged spectrophotometer 42. For example, as shown in FIG. 2, the processor 44 may be in wired or wireless communication with the highly abridged spectrophotometer 42, and the memory 46, the mixing model module 48, and the spectral data computing module 50 may be in wired or wireless communication with the processor 44. According to other embodiments, some system components may communicate with other system components in a different manner.

The highly abridged spectrophotometer 42 may be configured to measure, for example, reflectance of a sample at ten different wavelengths across the visual spectrum. However, one skilled in the art will recognize that the highly abridged spectrophotometer 42 may be configured to measure reflectance at more than or less than ten different wavelengths across the visual spectrum. The memory 46 may be any type of memory suitable for storing data generated by the highly abridged spectrophotometer 42, and data secured by other means.

The mixing model module 48 may be configured to determine an estimated weight of each spectral primary in the sample. According to various embodiments, depending on the particular production process, the mixing model module 48 may be a Neugebauer module, a single constant Kubelka Munk module, a two constant Kubelka Munk module, a log absorbance module, a multi-flux module, etc.

The spectral data computing module 50 may be configured to compute spectral data representative of the sample. For a given sample produced by a particular process, the values of the computed spectral data are based on spectral data for each spectral primary used in the production process and the estimated weight of each spectral primary in the sample.

As shown in FIG. 2, the system 40 may further comprise a spectral curve module 52 configured to generate a spectral curve representative of the sample based on the computed spectral data. According to various embodiments, the spectral curve module 52 may comprise a portion of the highly abridged spectrophotometer 42. According to other embodiments, the spectral curve module 52 may be separate and apart from the highly abridged spectrophotometer 42. For such embodiments, the spectral curve module 52 may be in wired or wireless communication with the processor 44 as shown in FIG. 2.

Each of the modules 48, 50, 52 may be implemented as software applications, computer programs, etc. utilizing any suitable computer language (e.g., C, C++, Delphi, Java, JavaScript, Perl, Visual Basic, VBScript, etc.) and may be embodied permanently or temporarily in any type of machine, component, physical or virtual equipment, storage medium, or propagated signal capable of delivering instructions to a device. The software code may be stored as a series of instructions or commands on a computer-readable medium such that when the processor 42 reads the medium, the functions described herein are performed.

As used herein, the term "computer-readable medium" may include, for example, magnetic and optical memory devices such as diskettes, compact discs of both read-only and writeable varieties, optical disk drives, and hard disk drives. A computer-readable medium may also include memory storage that can be physical, virtual, permanent, temporary, semi-permanent and/or semi-temporary. A computer-readable medium may further include one or more propagated signals, and such propagated signals may or may not be transmitted on one or more carrier waves.

Although the modules 48, 50, 52 are shown in FIG. 2 as three separate modules, one skilled in the art will appreciate that the functionality of the modules 48, 50, 52 may be combined into a single module. Also, although the modules 48, 50, 52 are shown as being part of a common system 40, the modules 48, 50, 52 may be installed on separate, distinct systems that are in wired or wireless communication with one another. For example, for embodiments where one or more of the modules 48, 50, 52 are installed on separate distinct systems, the modules may be in communication with one another via a network (not shown). Such a network may include any type of delivery system including, but not limited to, a local area network (e.g., Ethernet), a wide area network (e.g. the Internet and/or World Wide Web), a telephone network (e.g., analog, digital, wired, wireless, PSTN, ISDN, GSM, GPRS, and/or XDSL), a packet-switched network, a radio network, a television network, a cable network, a satellite network, and/or any other wired or wireless communications network configured to carry data. Such a network may also include elements, such as, for example, intermediate nodes, proxy servers, routers, switches, and adapters configured to direct and/or deliver data.

While several embodiments of the invention have been described, it should be apparent, however, that various modifications, alterations and adaptations to those embodiments may occur to persons skilled in the art with the attainment of some or all of the advantages of the disclosed invention. Therefore, this application is intended to cover all such modifications, alterations and adaptations without departing from the scope and spirit of the disclosed invention as defined by the appended claims.

What is claimed is:

1. A method for monitoring a process output with a highly abridged spectrophotometer, the method, comprising:
   securing spectral data for each spectral primary used in a process;
   measuring spectral data with a highly abridged spectrophotometer for a sample produced by the process;
   determining an estimated weight for each spectral primary in the sample;
   computing spectral data representative of the sample based on the secured spectral data and the determined estimated weight for each spectral primary in the sample; and
   storing the computed spectral data.

2. The method of claim 1, wherein securing the spectral data for each spectral primary used in the process includes measuring the spectral data with a benchmark instrument for each spectral primary used in the process.

3. The method of claim 2, wherein measuring the spectral data with the benchmark instrument comprises measuring the spectral data with a scanning spectrophotometer.

4. The method of claim 2, wherein measuring the spectral data with the benchmark instrument comprises measuring the spectral data with an abridged spectrophotometer that measures spectral data at thirty-one or more different wavelengths.

5. The method of claim 1, wherein measuring the spectral data with the highly abridged spectrophotometer includes measuring the spectral data for a predetermined number of different wavelengths.

6. The method of claim 5, wherein measuring the spectral data for the predetermined number of different wavelengths comprises measuring the spectral data for ten or fewer different wavelengths.

7. The method of claim 1, wherein determining the estimated weight for each spectral primary in the sample comprises determining each weight with a Neugebauer module.

8. The method of claim 1, wherein determining the estimated weight for each spectral primary in the sample comprises determining each weight with a one constant Kubelka-Munk module.

9. The method of claim 1, wherein determining the estimated weight for each spectral primary in the sample comprises determining each weight with a two constant Kubelka-Munk module.

10. The method of claim 1, wherein determining the estimated weight for each spectral primary in the sample comprises determining each weight with a log absorbance module.

11. The method of claim 1, wherein determining the estimated weight for each spectral primary in the sample comprises determining each weight with a multi-flux module.

12. The method of claim 1, further comprising determining an appropriate mixing module before securing the spectral data for each spectral primary used in the process.

13. The method of claim 2, further comprising storing the spectral data measured with the benchmark instrument.

14. The method of claim 1, further comprising storing the spectral data measured with the abridged spectrophotometer.

15. The method of claim 1, further comprising storing the estimated weight for each spectral primary in the sample.

16. The method of claim 1, further comprising generating a spectral curve that comprises the computed data points.

17. A system for monitoring a process output with a highly abridged spectrophotometer, the system comprising:
a highly abridged spectrophotometer;
a mixing model module for determining an estimated weight for each spectral primary in a sample based on spectral data measured by the highly abridged spectrophotometer; and
a spectral data computing module for computing spectral data representative of the sample based on the determined estimated weights.

18. A computer program stored on a computer-readable medium, the program comprising instructions for determining an estimated weight for each spectral primary in a sample produced by a process.

19. The computer program of claim 18, further comprising instructions for computing spectral data representative of a sample produced by a process, wherein the computed spectral data is based on the determined estimated weights.

20. The computer program of claim 19, further comprising instructions for generating a spectral curve based on the computed spectral data.

21. A method for monitoring a process output with a highly abridged spectrophotometer, the method, comprising:
securing spectral data for each base component used in a process, wherein the base component has a first spectrum that affects a spectrum of a sample produced by the process;
measuring spectral data for the sample with a spectrophotometer, wherein the spectrophotometer measures less than thirty-one (31) spectral bands across the visible spectrum;
determining an estimated weight for each base component in the sample;
computing spectral data representative of the sample based on the secured spectral data and the determined estimated weight for each base component in the sample; and
storing the computed spectral data.

22. A processor for monitoring a process output with a highly abridged spectrophotometer, wherein the processor is configured to:
receive spectral data for each spectral primary used in a process;
receive spectral data for a sample produced by the process, wherein the spectral data for the sample is measured with a highly abridged spectrophotometer;
determine an estimated weight for each spectral primary in the sample; and
compute spectral data representative of the sample based on the secured spectral data and the determined estimated weight for each spectral primary in the sample.

* * * * *